(12) United States Patent
Van Der Meulen et al.

(10) Patent No.: US 8,728,243 B2
(45) Date of Patent: May 20, 2014

(54) APPARATUS FOR EXTRACTION OF SACCHARIDES FROM LIGNOCELLULOSE MATERIAL BY MEANS OF HYDROLYSIS AND USE OF A CERTAIN MATERIAL IN THE APPARATUS

(75) Inventors: Torbjörn Van Der Meulen, Örnsköldsvik (SE); Gunnar Fransson, Bureå (SE); Lars Sundlöf, Skellefteå (SE); Jan Lindstedt, Örnsköldsvik (SE)

(73) Assignee: Sekab E-Technology AB, Ornskoldsvik (SE)

( * ) Notice: Subject to any disclaimer, the term of this patent is extended or adjusted under 35 U.S.C. 154(b) by 1045 days.

(21) Appl. No.: 12/450,014

(22) PCT Filed: Mar. 6, 2008

(86) PCT No.: PCT/SE2008/000182
§ 371 (c)(1),
(2), (4) Date: Sep. 8, 2009

(87) PCT Pub. No.: WO2008/108709
PCT Pub. Date: Sep. 12, 2008

(65) Prior Publication Data
US 2010/0135843 A1 Jun. 3, 2010

(30) Foreign Application Priority Data
Mar. 8, 2007 (SE) .................................... 0700578

(51) Int. Cl.
*C08B 30/00* (2006.01)
*C08B 37/00* (2006.01)
*C12P 7/10* (2006.01)

(52) U.S. Cl.
USPC ................ 127/36; 127/34; 435/165; 562/315

(58) Field of Classification Search
None
See application file for complete search history.

(56) References Cited

U.S. PATENT DOCUMENTS

| | | | |
|---|---|---|---|
| 4,523,928 A * | 6/1985 | Hillman et al. .................. 44/451 |
| 5,024,812 A | 6/1991 | Culling | |
| 5,411,594 A | 5/1995 | Brelsford | |
| 5,847,203 A | 12/1998 | Pennington | |
| 5,916,780 A * | 6/1999 | Foody et al. ..................... 435/99 |
| 6,090,595 A | 7/2000 | Foody et al. | |
| 6,878,212 B1 | 4/2005 | Pinatti | |
| 2003/0199049 A1 * | 10/2003 | Nguyen et al. ................. 435/165 |
| 2007/0148751 A1 * | 6/2007 | Griffin et al. .................. 435/161 |
| 2009/0118494 A1 * | 5/2009 | Blair et al. ..................... 536/127 |

FOREIGN PATENT DOCUMENTS

| | | |
|---|---|---|
| AT | GB 1449003 | 9/1976 |
| CN | 1117087 A | 2/1996 |
| CN | 1201832 | 12/1998 |
| EP | 0683241 A2 | 11/1995 |
| EP | 1 316 602 A2 | 6/2003 |
| EP | 1 361 290 | 11/2003 |
| EP | 1194226 B1 | 9/2004 |
| FR | 2197996 B1 | 11/1978 |
| RU | 2252977 * | 5/2005 |
| WO | WO 93/23359 A1 | 11/1993 |
| WO | WO 9323359 | 11/1993 |
| WO | WO 02/070753 A2 | 9/2002 |
| WO | WO 2006/086861 A2 | 8/2006 |

OTHER PUBLICATIONS

English translation of Chinese Office Action in corresponding Chinese Application No. 200880007078.9.
Davison et al., "Corrosion of Stainless Steel", Corrosion; (Metals Handbook) XP-002066422, Jan. 1, 1987, pp. 547-565.
Valentine, "Corrosion in the Pharmaceutical Industry", Metals Handbook, vol. 13. Corrosion, XP-055076949, Jan. 1, 1987, p. 1226.

* cited by examiner

*Primary Examiner* — Patricia L Hailey
*Assistant Examiner* — Sheng H Davis
(74) *Attorney, Agent, or Firm* — Birch, Stewart, Kolasch & Birch, LLP.

(57) ABSTRACT

The present invention relates to the use of a comparatively cheap material for the containment of at least a strongly acidic mineral acid solution highly diluted with water, by means of which saccharides are extracted from lignocellulose material by hydrolysis at a temperature of 175-240° C. and a pressure of 6-34 bar (0.6-14 MPa) as well as a time of 1-60 minutes and is characterized in that the material comprises, in addition to iron in an amount greater than any other individual substance and usually at least 50% by weight, at least chromium in an amount of 10.5-30% by weight, nickel in an amount of 2.5-29% by weight, and molybdenum in an amount of 0-7% by weight. The invention also relates to an apparatus.

6 Claims, No Drawings

APPARATUS FOR EXTRACTION OF SACCHARIDES FROM LIGNOCELLULOSE MATERIAL BY MEANS OF HYDROLYSIS AND USE OF A CERTAIN MATERIAL IN THE APPARATUS

TECHNICAL FIELD

The present invention bears upon a usage of a comparatively cheap material in an apparatus that is used in extraction of saccharides from lignocellulose material by means of hydrolysis. With hydrolysis is, in this connection, meant that certain substances are extracted from a material by means of an acid in the liquid state at a certain temperature and a certain pressure and during a certain time, i.e., it concerns an acid hydrolysis. The type of acids that comes in question in the hydrolysis are strong mineral acids and sulphur dioxide ($SO_2$), which are added to an aqueous solution in the form of a gas. Usual mineral acids are sulphuric acid, hydro-chloric acid and nitric acid. The lignocellulose material may be any known such material. One dominant among lignocellulose material is wood, which is found in deciduous trees as well as coniferous trees. A large number of other plants are also included in the concept lignocellulose material, such as bagasse, straw, hemp and corn stems. Materials produced from (based on) lignocellulose material, such as, for instance, waste paper, may also be a possibility as raw material.

The substances that are extracted from the lignocellulose material are saccharides in the form of pentoses as well as hexoses. When, among other things, the feedstock or raw material consists of wood, in any known form, such as sawdust, shavings of greater extension than sawdust and wood chips, hemicellulose is first released, which contains both pentoses and hexoses, and then cellulose in the form of glucose, which is a hexose.

PRIOR ART

There is a plurality of reasons for extracting saccharides from lignocellulose material. One is that the saccharides are used for production of ethanol via fermentation. It is since long (centuries) known that by means of yeast fungis convert hexoses to ethanol. Today, there are access to yeast fungis that convert pentoses to ethanol, i.e., the raw material base or feedstock for ethanol production need not today be limited to hexoses.

During relatively long time, saccharides from lignocellulose material have been extracted by means of acid hydrolysis under the usage of mineral acid highly diluted with water, for instance a sulphuric acid solution. Even if the concentrated acid is considerably diluted with water, the solution is strongly acidic, and therefore it has a low pH value, for instance within the interval of 0-4. In spite of water (in itself harmless from a corrosion point of view) being a dominant in the solution and usually amounts to at least 95% by weight, the solution is strongly corrosive and represents a danger to the material that contacts the acid solution. Reality is such that, for instance, concentrated sulphuric acid very well may be stored in a vessel made of common sheet iron (=cheap), but if the concentrated sulphuric acid is diluted with water, so that the amount of water constitutes, for instance, at least 95% by weight and the weak sulphuric acid solution is stored in the same vessel, this will quickly be destroyed by corrosion. Furthermore, it is so that the corrosion rate increases with temperature. Since those skilled in the art possess full knowledge of this, their hydrolysis vessels and also certain peripheral equipment have been manufactured from materials of a high quality from a corrosion point of view, which either are extremely expensive or very expensive. There are examples of hydrolysis vessels that have been manufactured entirely from zirconium, which is an extremely expensive material. Titanium and titanium alloys are other examples. Beryllium has also been proposed as a durable and therefore suitable material. In the category of very expensive materials, different alloys with nickel as a major constituent are included, i.e., the alloy consists of at least 30 (and often over 50) % by weight of nickel. There is a plurality of different names for such materials and also a plurality of different producers of the materials. Further down in this publication, some such materials are presented, with attached names.

Those skilled in the art have access to collections of tables, which indicate how different materials corrode under different conditions. One example of such a collection of tables is "Outokumpu Stainless Corrosion Handbook", 9th edition, 2004. On page II:59, there is data of interest in this connection. Different materials have been immersed in a sulphuric acid solution considerably diluted with water and having a temperature of 100° C., and the materials have been allowed to stay in this liquid environment for 168 h (7 days). The amount of sulphuric acid was 0.1% by weight and the solution had a pH value of 1.7. In the table denominated Sulphuric Acid $H_2SO_4$ on said page, the following two stainless steels, among others, are included; grade 18-10 (EN 1.4301, trade name=304) and grade 17-12-2.5 (EN 1.4436, trade name=316). (EN standard is an abbreviation of European standard.) The corrosion rate expressed in millimetre per year (mm/year) was in the respective case >1.0 and 0.1-1.0. For a material to be considered as corrosion resistant, the value should be below 0.1 mm/year. Already at a temperature of 100° C. of the acid solution, these two materials fall outside said grade concept. It is important to note that the measurements have been made on acid solutions as such and in absence of other chemicals.

Also in the extraction or rather the production of chemicals that entirely differ from saccharides, for instance aromatic carboxylic acids, there are corrosion problems that have forced the producers to manufacture reaction vessels from very expensive materials, for instance titanium. According to the international (PCT) patent application WO 93/23359, in the production of aromatic carboxylic acids, such as terephthalic acid, it is possible to replace at least certain parts of the reaction vessels from the very expensive materials titanium and titanium alloys to the considerably more cheaper material duplex stainless steel.

The production of the terephthalic acid takes place in such a way that an aromatic substance, such as paraxylene, in a reaction medium of a lower, aliphatic monocarboxylic acid, for instance concentrated acetic acid, in mixture with a low amount of water is oxidized in the presence of a mixture of the catalysts cobalt, manganese and bromine at a temperature within the interval of 180 to 220° C. and a pressure within the interval of 8 to 20 bar. The resulting chemical mixture with its contents of terephthalic acid is conveyed from the oxidation reactor to a series of crystallization vessels where the terephthalic acid is extracted and produced in pure form.

In the patent application, it is continuously warned of too a high amount or content of water in the reaction medium, which is harmful from a corrosion point of view. Furthermore, it is left open that the most critical parts of the apparatus or plant should be manufactured from the previously mentioned extremely expensive or very expensive materials.

This is proved by, for instance, the following text section in the patent application:

Page 5, line 24-page 6, line 2

"Furthermore, we do not exclude the possibility of parts of the plant and/or plant components being fabricated from two or more materials, including a duplex material and material which has superior corrosion resistance to the duplex steel under the conditions of operation. For instance, we have found that in certain parts of the plant, such as the oxidation reactor, the chemical composition may be particularly corrosive in the vapour phase as a result of the water constituent in the vapour phase being greater than in the liquid phase. In such a case, it may be preferable to fabricate that part of the plant, eg the oxidation reactor and/or the first crystalliser vessel, in such a way that those zones exposed to the liquid phase are constructed using duplex steel (or a lining thereof) whilst those zones exposed to the vapour phase and the interface between the liquid and vapour phases are constructed using a material having superior corrosion resistance (or a lining thereof), eg titanium, titanium alloy or a nickel-based alloy such as a suitable Hastelloy alloy."

Page 6, line 24-page 7, line 13

"The composition of the liquid phase mixture within the oxidation reactor vessel(s) typically comprises; 85-97% w/w acetic acid, 3-15% w/w water, 300-3000 ppm bromide concentration, 250-2000 ppm manganese content, 100-2000 ppm cobalt content and 0-250 ppm sodium content. Preferably the water content relative to the water/acetic acid content is from 3-10% w/w and the cobalt and manganese contents may each be up to 750 ppm. Usually of the bromine present in the oxidation reaction, a minor proportion thereof (typically about 20% to 30%) is in the ionic form. Surprisingly, the water content in the liquid phase mixture within the oxidation reactor has been found to be particularly important. We have found that the conditions prevailing in the vapour phase generated in the course of the oxidation reaction tend to be more severe than in the liquid phase and the main contributory factor in this respect has been identified as the water component present in the vapour. The amount of water present in the vapour phase is governed by the amount present in the liquid phase. By limiting the amount of water present in the liquid phase, it is possible to maintain the water content in the vapour phase at a level which permits the use of duplex steels in those parts of the reactor exposed to the vapour phase in operation. Accordingly in a preferred aspect of the invention, the water content of the liquid phase mixture in the oxidation reactor is maintained at a level not exceeding 8% w/w based on the water/acetic acid mixture, most preferably in the range 4 to 8% w/w. In this manner, it is possible to maintain the water content of the vapour phase within a range which makes the use of duplex steels in the vapour phase zone viable."

Page 8, lines 9-12,

"Experimental evidence obtained from electrochemical noise measurements of corrosion rate demonstrates that the corrosion rate of the 2507 alloy increases as the water content of a typical oxidation reactor composition increases but,"

ACCOUNT OF THE INVENTION

Technical Problem

As is clear from, among other things, what has been mentioned above, there is among those skilled in the art a unison fear, from a corrosion point of view, of handling liquids in the form of acids, and then not the least mineral acids, considerably diluted with water. Therefore, for instance, within the technical field of acid hydrolysis of lignocellulose material for extraction of saccharides, there has been a conviction that only high-quality materials and even extremely high-quality materials will do for the manufacture of reaction vessels etc., i.e., the apparatus in which the extraction of the saccharides takes place. The fact that these materials command a very high price has not only had the effect of hampering an industrial usage of the technology in question, but also, in some cases even, obstructing.

The Solution

The above-mentioned problem is solved by the present invention in the form of the use of comparatively cheap material for the containment of at least a strongly acidic mineral acid solution highly diluted with water, by means of which saccharides are extracted from lignocellulose material by hydrolysis at a temperature of 175-240° C. and a pressure of 6-34 bar (0.6-3.4 MPa) as well as a time of 1-60 min, characterized in that the material comprises, in addition to iron in an amount greater than any other individual substance and usually at least 50% by weight, at least chromium in an amount of 10.5-30% by weight, nickel in an amount of 2.5-29% by weight, and molybdenum in an amount of 0-7% by weight.

It is preferred that the material comprises, in addition to iron in an amount of at least 50% by weight, at least chromium in an amount of 15-26% by weight, nickel in an amount of 5-10% by weight, and molybdenum in an amount of 1.5-5.5% by weight.

The independent claims in this publication are, as is seen, written in an open form. With this is meant that the material that should be used is not described completely, i.e., the total number of included elements and the weight percentages thereof have not been defined, but on the other hand the elements that are dominating in terms of weight and importance. As regards molybdenum, which usually is an important element, it may in exceptional cases be omitted.

In said claims, the following four elements are defined and specified by amount; iron, chromium, nickel and molybdenum. In addition to said elements, the material may contain some few weight percentages of silicon and manganese as well as small amounts of carbon (at most 1.2%), nitrogen, sulphur and phosphorus. The are certain materials that deviate more or less as regards what just has been mentioned, and that, in spite of this, are comprised in the group of materials possible to be used according to the invention.

It falls within the general idea of the invention to limit the cost, in the severe conditions that prevail from a corrosion point of view in acid hydrolysis of lignocellulose material with the purpose of extracting saccharides, of the material of which the different parts of the system or apparatus consist, i.e., reaction vessels, material conveyors, pipes and so on, as much as possible, at the same time as the material resists the highly aggressive environment.

In general, it can be said that the greater amount of iron the material contains, the lower the production cost of the material will be.

It has surprisingly turned out that in this connection, among others, two commonplace and therefore comparatively cheap materials very well will do from a corrosion point of view, and it is duplex stainless steel and stainless steel.

In the group of stainless materials, all steel alloys are included having a content of chromium above 10.5%. The greatest group of stainless steels consists of austenitic stainless steels (usually called only stainless steels). Said steels are characterized in that they typically contain at least 50 percent by weight (%) of iron, 12-30% of chromium and 7-29% of nickel as well as some other metals/-substances, often molybdenum in 2-3%. The content of carbon in these steels is very low, generally below 0.05%. Stainless steel of this type is relatively simple to machine mechanically. They are formable and the low content of carbon makes it easier to weld in these materials than in many other types of stainless steel. Therefore, these austenitic stainless steels are used as structural steels and for pipe conduits. Acid-proof steels belong to this category of stainless steels.

Ferrite-austenitic stainless steels, also called duplex stainless steel, contain, in addition to iron of at least 50%, chromium up to 29%, nickel (5-8%), molybdenum (1-4%), carbon (below 0.03%) as well as nitrogen (approx. 0.4%). The material has a good corrosion resistance in environments with high contents of chloride, and a high mechanical strength, and is therefore suitable for, for instance, constructions at seacoasts. Duplex stainless steel has a higher strength than the previously described stainless steel. This combined with a good weldability and good workability means that the material is very suitable for different types of constructions.

Even if there is a plurality of materials that meet the criterion of the invention, i.e., that they are corrosion resistant in the described drastic reaction conditions and simultaneously comparatively inexpensive to produce and therefore also to purchase, here two duplex stainless steels, which meet said requirements, are accounted for in detail.

One of the duplex stainless steels is of the grade EN 1.4462 (trade name=2205) and has a specification (percentage by weight) of typically:
Phosphorus=0.02
Silicon=1.0
Carbon=0.02
Chromium=22
Nitrogen=0.17
Manganese=0.5
Molybdenum=3.1
Nickel=5.5
Sulphur=<0.01
Iron=67.7

The other duplex stainless steel is of the grade EN 1.4410 (trade name=SAF 2507) and has a specification (percentage by weight) of typically:
Phosphorus=0.02
Silicon=1.2
Carbon=0.02
Chromium=25
Nitrogen=0.28
Manganese=0.3
Molybdenum=3.9
Nickel=7
Sulphur=0.002
Iron=62.3

As is seen, in both cases, the amount of iron is above 60% by weight and in one case as high as 67.7% by weight.

The hydrolysis of the lignocellulose material may be effected in a plurality of ways. A suitable continuous way is described briefly below.

The raw material, for instance wood in chip form, is initially steamed. With steaming is meant that water steam is supplied to the chip pieces. This gives a good basis for the impregnation of the wood chips with a mineral acid solution, for instance a sulphuric acid solution. A suitable wood/liquid ratio is 1:3. After the acid impregnation, the wood chips and the acid solution are brought to a first reactor. It may be horizontal or vertical. In the first reactor, the hemicellulose portion of the lignocellulose material is decomposed into saccharides, pentoses and hexoses. To manage this, it is enough that the slurry contained in the reactor has a pH of 1.5-2.3 and that the temperature is 180° C., which gives a pressure of 10 bar. In a sulphuric acid solution having a pH of 1.5-2.3, the amount of sulphuric acid ($H_2SO_4$) is clearly less than 1% by weight. This means that the amount of water is more than 99% by weight. Suitable time of flow, i.e., treatment time, in this first reactor is 15 minutes. After the first reactor, the saccharides are washed out and brought to a collecting vessel. The reason for the saccharides being separated from the lignocellulose material suspension moving forward is that the released saccharides should not be subjected to the high temperature and high pressure and the low pH value of the acid solution that exist in the second reactor, where the previously released saccharides run the risk of being decomposed and destroyed. Since saccharide-containing suspension liquid has been separated from the lignocellulose material and conveyed away, the wood/liquid ratio is changed to 1:2. Additional sulphuric acid is added to the lignocellulose material suspension moving forward either before the second reactor or in connection with or a while after the material has been fed into the reactor. The addition of the sulphuric acid solution causes the wood/liquid ratio to increase somewhat from 1:2. This reactor may also be of horizontal or vertical type, but the last-mentioned type as the preferred one. In order to manage to decompose the cellulose remaining in the material into the saccharide glucose, it is not enough to increase the acid addition, which already has been described, but the temperature as well as the pressure have to be increased, for instance to about 200° C. or more, which gives a pressure of approx. 20 bar. A suitable pH value in the reactor is 1.7, and for this, a concentration of sulphuric acid of 0.1% by weight is required and then the balance is water. Suitable time of flow, i.e., treatment time, in this second reactor is 10 minutes.

The total treatment time in the above described hydrolysis method amounts to 25 minutes. The treatment time in the individual case may vary within the interval previously mentioned and is, among other things, depending on if one, two or three hydrolysis steps are used and what temperature that is selected in the individual step. In the case of very short treatment times, i.e., in the region of 1 minute, the lignocellulose material is subjected to steam explosion treatment for the extraction of the saccharides.

The remaining lignocellulose material, which may be called lignin material or lignin residue, is conveyed together with the chemical (including glucose) containing suspension liquid from the second reactor to previously mentioned collecting vessel. In the following dewatering step, the lignin residue is separated from the saccharide-containing suspension liquid, which also may be called hydrolyzate. A suitable apparatus in the dewatering step is a membrane filter press, but also another type of equipment can be used. Plug screws are used to convey the lignocellulose/lignin material between the different treatment or reaction steps. Sometimes the conveyance is combined with dewatering. Said plug screws also work as pressure locks between the different treatment vessels.

It is also possible to combine the two hydrolysis steps with a third step where saccharides are extracted from the lignocellulose material by means of enzymes. Yet a possibility is to combine a prehydrolysis step with acid followed by an enzymatic cellulose hydrolysis. In any case, finally there are obtained a solid phase, having a solid content of about 40% in the form of the lignin residue (dry solids content above 50% and the fraction of lignin residue from the wood of approx. 40%), as well as a liquid phase, which contains the desired saccharides. The subsequent actual use of the saccharides is a choice of the producer of the saccharides. The most common field of use is ethanol production. The lignin residue may come to use in combustion, so that the energy content thereof is taken care of. As regards the lignin residue, there are also alternative fields of use. For instance, pellets may be produced and in addition, the lignin may constitute base raw material for the production for a plurality of useful products. The hydrolysis treatment of lignocellulose material does not necessarily have to be carried out continuously, on the contrary nothing prevents that the treatment is carried out batchwise, i.e., discontinuously.

The above listed apparatus parts, for instance the two reactors and other vessels, plug screws, dewatering apparatuses and pipe conduits or more precisely all apparatuses that come into contact with the considerably acidic acid solution highly diluted with water, have to overcome the corrosion problems. This is irrespective of whether it is the lignocellulose material plus the suspension liquid that are contained or only one of these material flows that is contained. As has been described previously, it occurs, among other things, that a certain amount of liquid is separated from the suspension and is further conveyed separately. In most cases it is the entire mixture, i.e., the lignocellulose material plus the acid solution that fairly quickly are transformed into a suspension liquid containing a large number of chemical substances, that is contained.

It has previously been indicated that the comparatively cheap material stainless steel actually and very surprisingly resists the described conditions that are highly aggressive from a corrosion point of view, and that it is fully possible to manufacture also the most attacked, as regards corrosion, hydrolysis reactor from such a sheet-metal material. It may be possible to further reduce the cost of the material by combining stainless steel with an even more cheaper support material and where the layer of stainless steel is facing inward and consequently is brought into contact with, for instance, the highly aggressive acid solution.

The invention also comprises the apparatus category and reference is made to the claims found in the end of this publication.

Advantages

From a large number of test runs (accounted for in the embodiment example further below in the publication), it is clear that a plurality of types of stainless steel resist the aggressive conditions from a corrosion point of view that prevail in acid hydrolysis of lignocellulose material with the purpose of extracting saccharides, which later can be used for, for instance, the production of ethanol. The corrosion resistance of several stainless steels is not far from the corrosion resistance of several nickel-based alloys. As regards one case of nickel-based alloy, the corrosion resistance thereof is even clearly inferior to the corrosion resistance of the stainless steels.

Some of the nickel-based alloys having high corrosion resistance are recognized under the trade name Hastelloy. Hastelloy C-276, for instance, commands a price that is about four times as high as the price of a duplex stainless steel that is preferred according to the invention, viz. EN 1.4462 having the trade description 2205.

Since several hundred tons of materials are needed to construct the described apparatus, replacing the nickel-based alloy, for instance Hastelloy C-276, by the stainless steel EN 1.4462 will imply a saving of SEK X·100 millions in construction cost of the plant or apparatus. The numerical value of X depends on the production capacity of the plant or apparatus assembly, type of included apparatuses etc. Extremely expensive materials, as for instance zirconium, command a price of at least twice the price of Hastelloy C-276.

A question that is most relevant to ask oneself is if there is some explanation to the fact that the stainless steel in one case, i.e., when it is surrounded by an aqueous solution supplied with 0.1% by weight of sulphuric acid resulting in a pH of the solution of 1.7, exhibits a significant corrosion already at a temperature of the sulphuric acid solution of 100° C., while the stainless steel in the other case, i.e., when it is surrounded by essentially the same sulphuric acid solution, exhibits a significant corrosion resistance in spite of the temperature of the sulphuric acid solution amounting to 210° C. Some scientifically verified explanation to this does not exist but only astonishment and surprise. One speculation and theory is that since the sulphuric acid solution in the second case not only consists of sulphuric acid and water but also of smaller and greater amounts of different chemical substances that have released from the lignocellulose material, it is very likely that one or more of said released substances work as protective agent (protector) for the stainless steel plate.

BEST EMBODIMENT

What is mentioned under this heading is in this case limited to very detailed tests, which are accounted for in the example below.

EXAMPLE 1

Ten different materials were tested, five were different types of stainless steels and five were nickel-based alloys expected to be of a high quality from a corrosion point of view. From each material, two types of samples were made. One of the types of sample had the measures: length=150 mm, width=40 mm and the thickness of 2.5 mm. 30 mm from one of the short sides, there was centrally recessed a bore hole having a diameter of 12 mm. 60 mm from the other short side, a welding seam was applied. The second type of sample had the measures: length=80 mm, width 20 mm and the thickness of 2.5 mm. At a distance from the two short sides, a respective hole was centrally recessed having a diameter of 10 mm. The distance between the centres of the two holes was 50 mm. Next, the plane, rectangular sample was bent together so that to a u-shape was formed. The first-mentioned plane samples and the u-shaped samples were degreased. After careful weighing of each one of the samples, these were placed in a rig consisting of three threaded bars projecting from an end portion of an autoclave. The holes recessed in the samples made it possible to thread down the samples along the bars. One bar was used for the plane samples, while the u-shaped samples required two bars in order to get room. Shims were inserted between the samples.

In the case of the u-shaped samples, the shims were nuts, which allowed a certain compression of the u-shaped samples. It was proceeded in such a way in order to obtain knowledge about if a material stress affected the corrosivity of the material. Four samples of each material were applied to the rig, two plane ones and two u-shaped ones.

The heart of the test apparatus consisted of a cylindrical autoclave, the two end portions of which were openable and closeable. Said rig including the samples was introduced into the autoclave, and then it was closed. The autoclave was jacketed and the jacket contained electrical elements so that the temperature inside the autoclave could be set at a desired level. The rest of the test apparatus consisted of a pipe system for circulation of the acid solution, some tanks serving as retention vessels for the acid solution, a high-pressure pump, a high-pressure valve and a three-way valve. The apparatus system also contained a preheater just before the autoclave and a cooling device just behind the autoclave as well as a particle filter behind the same, and finally there was a pressure vessel containing nitrogen connected to the pipe system for pressure regulation. All parts that were exposed to the acid solution consisted of the material Hastelloy C-276.

The storage tanks were provided with a sulphuric acid solution considerably diluted with water in the form of a saccharide-containing hydrolyzate, collected in a pilot plant for extraction of saccharides from wood chips. The pH value of the hydrolyzate was 1.67. The content thereof of chloride was analysed and it amounted to <5 ppm. That content was considered as low in comparison with what was expected to occur under industrial conditions, and therefore sodium chloride (NaCl) was added so that the content of chloride increased to 49 ppm.

The circulation of the hydrolyzate was started and the autoclave was set at a temperature of 210° C. and a pressure of 35 bar. This high pressure was used to avoid the formation of water vapour. The experiment continued for 13 days after which the previously mentioned rig including the samples was, subsequent to cooling, unloaded from the autoclave. The samples were disconnected and carefully cleaned, after which the same were weighed again. The difference between the original weight and the weight after the experiment was the amount or weight of material that had disappeared, i.e., corroded away. Based on this numerical value in gram, the degree of corrosion was calculated expressed in millimetre per year.

In Table 1 below, the results have been compiled. In this, only the plane samples have been included (double samples).

TABLE 1

| Material trade designation or trade name | Grade design. EN No. | Sample No. | Orig. weight g | Final weight g | Diff. g | Degree of corrosion mm/year |
|---|---|---|---|---|---|---|
| 316 | 1.4436 | 1.2 | 81.3142 | 81.1590 | 0.1552 | 0.0460 |
|  |  | 1.3 | 81.6056 | 81.4530 | 0.1526 | 0.0452 |
| 2205 | 1.4462 | 2.1 | 76.9504 | 76.9085 | 0.0419 | 0.0124 |
|  |  | 2.2 | 76.9830 | 76.8945 | 0.0885 | 0.0262 |
| 904 | 1.4539 | 3.1 | 84.6858 | 84.5463 | 0.0895 | 0.0265 |
|  |  | 3.2 | 85.6471 | 85.5518 | 0.0953 | 0.0282 |
| 254 SM0 | 1.4547 | 4.1 | 82.1804 | 82.1330 | 0.0474 | 0.0140 |
|  |  | 4.2 | 82.7743 | 82.7179 | 0.0564 | 0.0167 |
| SAF 2507 | 1.4410 | 5.1 | 80.9039 | 80.8469 | 0.0570 | 0.0169 |
|  |  | 5.2 | 79.9447 | 79.9026 | 0.0421 | 0.0125 |
| Inconel 600 | 2.4816 | 6.1 | 86.0582 | 85.7532 | 0.3230 | 0.0957 |
|  |  | 6.2 | 86.4785 | 86.9001 | 0.3784 | 0.1121 |
| Hastelloy C4 | 2.4610 | 7.1 | 90.9217 | 90.9213 | 0.0004 | 0.0001 |
|  |  | 7.2 | 91.6377 | 91.6230 | 0.0147 | 0.0044 |
| Alloy 59 | 2.4605 | 8.1 | 90.3612 | 90.3431 | 0.0181 | 0.0054 |
|  |  | 8.2 | 89.7062 | 89.7061 | 0.0001 | 0.0000 |
| Hastelloy C-276 | 2.4819 | 9.1 | 90.2588 | 90.2444 | 0.0144 | 0.0043 |
|  |  | 9.2 | 89.9583 | 89.9464 | 0.0119 | 0.0035 |
| Inconel C-276 | 2.4819 | 10.1 | 86.9105 | 86.8704 | 0.0401 | 0.0119 |
|  |  | 10.2 | 86.8981 | 86.8725 | 0.0256 | 0.0076 |

The five first materials in the table above are examples of stainless steels. As has been indicated previously, materials having a degree of corrosion below 0.1 mm/year are termed corrosion resistant. All five stainless steels meet this, since the degree of corrosion of all these materials is clearly less than said numerical value. The best result among said five stainless steels have those with the trade names 2205, 254 SMO and SAF 2507 (their EN numbers are seen in the above table), and therefore a usage of some of these materials is preferred according to the invention.

The only one of the tested materials not being corrosion resistant is the material with the trade name Inconel 600, which is a nickel-based alloy and therefore commands a price of the order of four times the price of stainless steels.

The other materials within the group of nickel-based alloys are doubtless corrosion resistant.

As regards the samples that were subjected to a mechanical pressure or mechanical stress, i.e., the u-shaped samples, it was found that no one of the samples had alarming problems with pitting.

Among the ten studied materials of the first set of testing and the results of which is seen in Table 1, five promising materials were selected for further corrosion studies. In addition, a sixth material was studied in the form of the stainless steel having the grade designation EN 1.4301. This material is regarded as a low-grade stainless steel. The samples for the second experiment were made simultaneously with the samples for the first experiment. The same equipment and the same method were used in the second experiment as in the first experiment except for the time of exposure being increased to 34 days.

In Table 2 below, the results have been compiled.

TABLE 2

| Material trade designation or trade name | Grade design. EN No. | Sample No. | Degree of corrosion mm/year |
|---|---|---|---|
| 304 | 1.4301 | A | 0.0165 |
|  |  | B | 0.0129 |
| 2205 | 1.4462 | 2 | 0.0072 |
|  |  | 2.3 | 0.0069 |
|  |  | 2.4 | 0.0057 |
|  |  | 2.5 | 0.0077 |
| 254 SMO | 1.4547 | 4.3 | 0.0019 |
|  |  | 4.4 | 0.0031 |
|  |  | 4.5 | 0.0031 |
| SAF 2507 | 1.4410 | 5 | 0.0055 |
|  |  | 5.3 | 0.0065 |
|  |  | 5.4 | 0.0070 |
|  |  | 5.5 | 0.0070 |
| Alloy 59 | 2.4605 | 8.3 | 0.0019 |
|  |  | 8.4 | 0.0004 |
| Hastelloy C-276 | 2.4819 | 9.0 | 0.00014 |
|  |  | 9.3 | 0.00051 |

As is seen, the degree of corrosion of all materials is below the critical limit of 0.1 mm/year by a great margin, which means that all materials are classified as corrosion resistant. Surprisingly enough, the corrosion is minimal also for the relatively simple stainless steel EN 1.4301 (trade name 304). The fact that the very expensive nickel-based alloys Alloy 59 and Hastelloy C-276 have good results is not surprising, but expected.

In conclusion, it can be established from the results attained and accounted for in the two tables above that it surprisingly turned out that two commonplace and therefore comparatively inexpensive materials, i.e., duplex stainless steel and stainless steel, will do well from a corrosion point of view in the extraction of saccharides from lignocellulose material by means of acid hydrolysis.

The invention claimed is:

1. A method of industrial extraction of saccharides from a lignocellulose material in a plant, comprising:
   performing hydrolysis on the lignocellulose material by contacting the lignocellulose material with an acidic water solution using an apparatus for large scale industrial extraction, which is part of the plant, where the acidic water solution is a sulfur dioxide solution or a sulfuric acid solution,
   wherein the at least one part of the apparatus includes stainless steel or duplex stainless steel, and
   wherein the acidic water solution has a pH of 1.5 to 2.3 and a temperature of 175° C. to 240° C.

2. The method of claim 1, wherein the stainless steel is austenitic stainless steel.

3. The method of claim 1, wherein the at least one part includes at least one selected from the group consisting of reaction vessels, material conveyors, pipes, plug screws, pipe conduits and dewatering apparatuses.

4. The method of claim 1, wherein the acidic water solution has a temperature of 175° C. to 210° C.

5. A method of industrial hydrolysis of the lignocellulose material, comprising:
   performing prehydrolysis on the lignocellulose material according to claim 1 using an acid; and
   performing enzymatic cellulose hydrolysis on the prehydrolyzed lignocellulose material.

6. A method of industrial production of ethanol, comprising:
   performing the method according to claim 1, wherein the ethanol is produced from the lignocellulose material.

* * * * *